(12) United States Patent
Kask et al.

(10) Patent No.: US 6,965,113 B2
(45) Date of Patent: Nov. 15, 2005

(54) FLUORESCENCE INTENSITY MULTIPLE DISTRIBUTIONS ANALYSIS: CONCURRENT DETERMINATION OF DIFFUSION TIMES AND MOLECULAR BRIGHTNESS

(75) Inventors: Peet Kask, Harjumaa (EE); Stefan Jäger, Hamburg (DE); Kaupo Palo, Haabneeme (EE); Ülo Mets, Tallinn (EE); Karsten Gall, Lunestedt (DE)

(73) Assignee: Evotec AG, Hamburg (DE)

( * ) Notice: Subject to any disclaimer, the term of this patent is extended or adjusted under 35 U.S.C. 154(b) by 233 days.

(21) Appl. No.: 09/779,461

(22) Filed: Feb. 9, 2001

(65) Prior Publication Data

US 2002/0008211 A1 Jan. 24, 2002

Related U.S. Application Data

(60) Provisional application No. 60/181,564, filed on Feb. 10, 2000.

(51) Int. Cl.[7] .............................................. G01N 21/64
(52) U.S. Cl. ..................................... 250/459.1; 702/28
(58) Field of Search .......................... 250/459.1; 702/28

(56) References Cited

U.S. PATENT DOCUMENTS

| | | | |
|---|---|---|---|
| 4,198,571 A | 4/1980 | Sheppard | 250/216 |
| 5,866,911 A | 2/1999 | Baer | 250/458.1 |
| 6,208,815 B1 * | 3/2001 | Seidel et al. | 396/337 |
| 6,222,664 B1 * | 4/2001 | Dorsel | 359/227 |
| 6,376,843 B1 * | 4/2002 | Palo | 250/458.1 |
| 6,515,289 B1 * | 2/2003 | Kask | 250/459.1 |

FOREIGN PATENT DOCUMENTS

| | | | |
|---|---|---|---|
| EP | 0 836 090 A1 | 4/1998 | |
| EP | 884583 A1 * | 12/1998 | G01N/21/64 |
| WO | WO 98/23941 | 6/1998 | |

OTHER PUBLICATIONS

Hong Oian et al., "On The Analysis of High Order Moments of Fluorescence Fluctuations", vol. 57, pp. 375–380, Feb. 1990, Biophys. J.

* cited by examiner

*Primary Examiner*—David Porta
*Assistant Examiner*—Shun Lee
(74) *Attorney, Agent, or Firm*—Jacobson Holman PLLC (57) ABSTRACT

A method for distinguishing samples having flourescent particles includes (a) monitoring intensity fluctuations of fluorescence emitted by the particles in at least one measurement volume by detecting sequences of photon counts by at least one photon detector, (b) determining, from the sequences of photon counts, intermediate statistical data involving at least two probability functions of the number of photon counts detected in different sets of counting time intervals, and (c) determining from the intermediate statistical data a distribution of particles as a function of at least two arguments, wherein one argument is a specific brightness of the particles, or a measure thereof, and another argument is a diffusion coefficient of the particles, or a measure thereof.

19 Claims, 6 Drawing Sheets

FLUORESCENCE INTENSITY MULTIPLE DISTRIBUTIONS ANALYSIS: CONCURRENT DETERMINATION OF DIFFUSION TIMES AND MOLECULAR BRIGHTNESS

This application claims priority from and the benefit of U.S. Provisional Application Ser. No. 60/181,564, filing date Feb. 10, 2000.

The present relates to a method for characterizing samples having fluorescent particles, said method being based on the concurrent determination of diffusion times and specific brightnesses, or measures thereof.

Fluorescence correlation spectroscopy (FCS) has proven to be a technique with single molecule sensitivity. Magde et al. (Phys. Rev. Lett. 29; 704–708, 1972) demonstrated the feasibility of detecting molecular number fluctuations by fluorescence correlation spectroscopy. Since then an increasing number of publications has appeared, aimed at improving the performance and accuracy of this technique. A progress was the implementation of confocal detection optics (Koppel et al., Biophys. J. 16: 1315–1329, 1976; Rigler and Widengren, BioScience 40: 180–183, 1990) and the use of silicon photon detectors (Rigler et al., Eur. Biophys. J. 22: 169–175, 1993). This development pushed the detection limit below the single-molecule level (Rigler et al., In: Fluorescence Spectroscopy: New Methods and Applications. O. S. Wolfbeis, editor. Springer Berlin. 13–24, 1993; Eigen and Rigler, Proc. Natl. Acad. Sci. USA 91: 5740–5747, 1994; Brand et al., J. Phys. Chem. 101: 4313–4321, 1997; Eggeling et al., Proc. Natl. Acad. Sci. USA 95: 1556–1561, 1998).

In recent publications comprising fluorescence fluctuation spectroscopy the attention has been drawn towards analyzing the histogram of the number of photon counts rather than the autocorrelation function (Qian and Elson, Biophys. J. 57: 375–380, 1990; Fries et al., J. Phys. Chem. 102: 6601–6613, 1998; Chen et al., Biophys. J. 77: 553–567, 1999; Kask et al., Proc. Natl. Acad. Sci. USA 96: 13756–13761, 1999). Lately, FCS has found a complement in the form of fluorescence intensity distribution analysis (FIDA); FIDA has been introduced as a method for analyzing mixtures of fluorescent particles. It is based on the detection of instantaneous photon emission rates from an open confocal volume. Central part of the method is the collection of photon count numbers, recorded in time intervals of fixed duration (time windows) and using this information to build up a count number histogram. A theoretical probability distribution of photon count numbers is fitted against the obtained histogram yielding specific brightness values, q, as well as concentrations, c, for all different species in the sample. The term "specific brightness" generally denotes the mean count rate of the detector from light emitted by a particle of given species situated in a certain point in the sample, conventionally in the point where the value of the brightness profile function is unity.

The historic predecessor of FIDA is FCS, which distinguishes different species on the basis of their characteristic diffusion times $\tau$, by analyzing the second order autocorrelation function of light intensity, $G(t)=(I(0)I(t))-(I)^2$. Parameters which can be determined by FCS (in addition to diffusion times $\tau$) are not, however, concentrations and specific brightness values of different species separately, but products of the form $cq^2$. While fluorescence intensity distribution analysis (FIDA) relies on a collection of instantaneous values of the fluctuating intensity, FCS analyzes the temporal characteristics of the fluctuations. Hence, the two methods represent complementary tools: FCS resolves components with different diffusion coefficients, while FIDA distinguishes the species according to their different values of specific molecular brightness.

The present invention is aimed at developing a method that not only unifies the advantages of both techniques, but rather yields a synergistic effect.

According to the present invention, a new fluorescence fluctuation method is introduced that is based on the global analysis of a set of photon count number histograms, recorded with preferably multiple widths of counting time intervals simultaneously. This Fluorescence Intensity Multiple Distributions Analysis (FIMDA) distinguishes fluorescent species on the basis of both, the specific brightness and the translational diffusion time. The combined information, extracted from a single measurement, increases the read-out effectively by one dimension and thus breaks the individual limits of prior art techniques, i.e. FCS and FIDA. FIMDA can be widely applied for monitoring molecular interactions including receptors and ligands or antibodies and antigens, which are both of great relevance in the life sciences.

The present invention describes the dependence of photon count number distributions on diffusion coefficients and applies it to a series of photon count number histograms corresponding preferably to different widths of counting time intervals. In the following, sometimes the wording "experimentally determined distribution function" or "experimentally determined distribution" will be used instead of "histogram". As explained, the key is to analyze a set of distributions which is sensitive to the translational diffusion of particles. FCS detects the dynamics of particles, because it compares the instantaneous intensities at time intervals separated by a certain delay In order to make the distribution of photon count numbers sensitive to the temporal evolution of intensity one may alternatively— according to the present invention—choose to build a set of photon count number distributions corresponding to different time windows. The choice of the time windows should preferably span a range comparable to the delay values used in FCS.

In contrast to other two-dimensional FIDA techniques (Kask et al., Biophys. J. 78, 2000), which use two detectors, in FIMDA only a single detector is needed, though multiple detectors might be used.

While the ability of the method according to the present invention to determine specific brightness values, diffusion times, and concentrations from mixtures is demonstrated on simulated data, its experimental utilization is shown by the determination of the binding constant of a protein-ligand interaction exemplifying its broad applicability in the life sciences. Since the values for all three parameters, i.e. brightness, diffusion and concentration, can be attributed to each species, the method according to the present invention is a more powerful tool of analysis than applying FCS and FIDA separately. The statistical accuracy of each extracted parameter determined according to the present invention is comparable to that in FCS or FIDA, often even better.

In the following, a modification of the theory of FIDA is presented, which is a suitable approximation for experimental purposes. In FIDA, a convenient representation of a photon count number distribution $P(n)$ is its generating function, defined as $$R_{P(n)}(\xi) = \sum_n \xi^n P(n). \tag{1}$$

The simple theory of FIDA assumes (i) that molecules are immobile during the counting time interval, and (ii) that the light flux from a molecule can be expressed as a product of a spatial brightness function $B(r)$ (this is a function of spatial coordinates of the molecule characterizing the equipment) and a specific brightness q (characterizing a certain molecule species). Under these two assumptions, the distribution of the number of photon counts, emitted by molecules from a volume element dV is double Poissonian and the corresponding generating function reads $$R_{P(n)}(\xi) = \exp[cdV(e^{(\xi-1)qB(r)T}-1)], \tag{2}$$

where $\xi$ is the complex argument of the generating function, c is the concentration of molecules, and T is the width of the counting time interval. The representation is particularly convenient, because contributions from independent sources, like different volume elements or species, are combined by simple multiplication of the contributing generating functions. The generating function of $P(n)$ for a single species is $$R_{P(n)}(\xi) = \exp[c\int(e^{(\xi-1)qB(r)T}-1)dV], \tag{3}$$

while accounting for multiple species simply yields $$R_{P(n)}(\xi) = \exp\left[\sum_i c_i \int (e^{(\xi-1)q_iB(r)T} - 1)dV\right]. \tag{4}$$

The integral on the right hand side of Eq. 4 is calculated numerically, but instead of the three-dimensional integration over spatial coordinates, a one-dimensional integration coordinate $x = \ln|B_0/B(r)|$ is introduced. The relationship between the brightness B and the coordinate x is therefore $B(x)=B_0 e^x$. In FIDA it is suitable to express the function dV/dx, which describes the brightness profile in one-dimensional representation, by the formula:

$$\frac{dV}{dx} = A_0(1 + a_1 x + a_2 x^2)x^{a_3} \tag{5}$$

Here $a_1$, $a_2$ and $a_3$ are empirical adjustment parameters granting for a sufficient flexibility to fit the measured histograms with high precision. However, a representation in the form $$\frac{dV}{dx} = A_0(x + a_1 x^2 + a_2 x^3)$$

might also be used. The selection of coefficients $A_0$ and $B_0$ is nothing but the selection of the units of V and B. Usually, they are determined from the conditions $$\int B dV = 1, \tag{6}$$

$$\int B^2 dV = 1. \tag{7}$$

So far, a simple version of the theory of FIDA has been described. For the purposes of FIMDA according to the present invention, one has to abandon the assumption that molecules are immobile during the counting interval. Surprisingly, according to the present invention one does not abandon Eq. 2, as well as the following equations, but one will redefine the meaning of some variables instead. x is still a variable related to the spatial brightness profile, but now it characterizes the path of the molecule rather than its position. B is the spatial brightness averaged over the path rather than determined at a fixed position of the molecule. V is not the volume in space but dV/dx still expresses the probability that a molecule has a given value of x. If one would keep the original meaning of c and q, one would have to develop a theory predicting how $A_0$, $a_1$, $a_2$ and $a_3$ depend on the counting time interval T. However, according to the present invention another approach has been chosen. The normalization conditions have been kept (Eqs. 6 and 7) and it was even found possible to apply a single section of the values $A_0$, $a_1$, $a_2$ and $a_3$ for a set of different time windows. The consequence of this selection is that in Eqs. 2–4 c is an apparent concentration ($c_{app}$) and q is an apparent brightness ($q_{app}$) which both depend on the width of the counting time interval T.

In the following, a theory is presented predicting how $c_{app}$ and $q_{app}$ depend on T. The case of single species is studied and the first and the second factorial cumulants of the distribution corresponding to Eq. 3 are calculated. The factorial cumulants are defined as $$K_n = \left(\frac{\partial}{\partial \xi}\right)^n \ln(R(\xi))\bigg|_{\xi=1} \tag{8}$$

yielding:

$$K_1 = \langle n \rangle = c_{app} q_{app} T, \tag{9}$$

$$K_2 = \langle n(n-1) \rangle - \langle n \rangle^2 = c_{app} q_{app}^2 T^2, \tag{10}$$

where normalization conditions given by Eqs. 6 and 7 have been used. (Note that Eqs. 9 and 10 are in total agreement with Qian and Elson's formulae (Biophys. J. 57: 375–380, 1990) derived under the assumptions i and ii.) From Eq. 9 one can conclude that $$c_{app}(T)q_{app}(T) = \langle I \rangle, \tag{11}$$

where $\langle I \rangle = \langle n \rangle_T / T$ is the mean count rate, which does not depend on the choice of T. One shall proceed by employing the following relationship between the second cumulant of the count number distribution $P(n;T)$ and the autocorrelation function of fluorescence intensity $G(t) = \langle I(0)I(t) \rangle - \langle I \rangle^2$, $$\langle n(n-1) \rangle_T - \langle n \rangle_T^2 = \int_0^T dt_1 \int_0^T dt_2 G(t_2 - t_1). \tag{12}$$

Introducing the notation $$\Gamma(T) = \frac{1}{c_{app}(0)q_{app}^2(0)T^2} \int_0^\tau dt_1 \int_0^\tau dt_2 G(t_2 - t_1), \quad (13)$$

one gets from Eqs. 12 and 10

$$c_{app}(T)q_{app}^2(T) = c_{app}(0)q_{app}^2(0)\Gamma(T). \quad (14)$$

From Eqs. 11 and 14 one gets $$c_{app}(T) = \frac{c_{app}(0)}{\Gamma(T)}, \quad (15)$$

$$q_{app}(T) = q_{app}(0)\Gamma(T), \quad (16)$$

As the concluding step in the theory underlying the present invention, one shall substitute the expressions of G(t) from FCS into Eq. 13. If one ignores triplet trapping and studies pure diffusion, then $c_{app}(0)$ is the true concentration c, and $q_{app}(0)$ is the true specific brightness q. Applying a Gaussian brightness function (Aragón and Pecora, J. Chem. Phys. 64: 1791–1803, 1976), the autocorrelation function is $$G_{diff}(t) = cq^2 \left(1 + \frac{D|t|}{\sigma_r^2}\right)^{-1} \left(1 + \frac{D|t|}{\sigma_z^2}\right)^{-1/2}, \quad (17)$$

denoting D as the diffusion coefficient and $\sigma_r$ as the radial and $\sigma_z$ as the longitudinal distance, where the Gaussian profile has dropped $e^{1/2}$ times. The integrals in Eq. 13 yield the correction factor for translational diffusion $$\Gamma_{diff}(t) = \frac{4}{t^2\beta\sqrt{1-\beta}} \left[\beta(1+f)\text{artanh}\left(\frac{\sqrt{1-\beta}(\sqrt{1+\beta f}-1)}{\beta + \sqrt{1+\beta t}-1}\right) - \sqrt{1-\beta}(\sqrt{1+\beta t}-1)\right], \quad (18)$$

where $t = DT/\sigma_r^2$ and $\beta = \sigma_r^2/\sigma_z^2$. For reasons explained below it is useful to calculate the first order terms in Eq. 18:

$$\Gamma_{diff}(T) = \left[1 + \frac{DT}{6}\left(\frac{2}{\sigma_r^2} + \frac{1}{\sigma_z^2}\right)\right]^{-1} + O(D^2). \quad (19)$$

However, from theoretical considerations as well as from measurements it is known that simple physical models like Gaussian or else Gaussian-Lorentzian do not exactly represent the actual brightness profile (Kask et al., Proc. Natl. Acad. Sci. USA 96: 13756–13761, 1999). Therefore, according to the present invention a modified Eq. 19 has been used and a fitting parameter a has been introduced, that preserves the first order terms in Eq. 19:

$$\Gamma_{diff}(T) \approx \left[1 + \frac{DT}{6a}\left(\frac{2}{\sigma_r^2} + \frac{1}{\sigma_z^2}\right)\right]^{-a}. \quad (20)$$

By matching the second order terms the Gaussian brightness profile would correspond to a=⅔, but we rather choose a to be an empirical parameter, which can be determined by the fitting procedure. From Eqs. 15 and 16 one can express the apparent parameters of a pure diffusion process:

$$c_{app}^{(diff)}(T) = \frac{c}{\Gamma_{diff}(T)}, \quad (21)$$

$$q_{app}^{(diff)}(T) = q\Gamma_{diff}(T). \quad (22)$$

Another phenomenon involved is that of intensity fluciuations due to trapping of molecules into triplet excited state (Widengien et al., J. Phys. Chem. 99, 1368–13379, 1995). To obtain a good fit, particularly at values of T comparable to the triplet lifetime (which is typically 2 μs), an additional factor has been introduced into G(r):

$$F_{trip}(t) = \frac{1 + \kappa\tau \exp\left(-\frac{(1+\kappa\tau)|t|}{\tau}\right)}{(1+\kappa\tau)^2}, \quad (23)$$

where κ is the singlet to triplet transition rate and τ is the triplet lifetime. As the following step, one may consider Eq. 23 with an additional factor of $cq^2$ as a correlation function of an ensemble of immobile particles undergoing triplet transactions:

$$G_{trip}(t) = cq^2 F_{trip}(t) \quad (24)$$

From Eq. 13 and 24 on can compute:

$$\Gamma_{trip}(T) = \frac{\left\{2\frac{\tau}{T}\kappa\tau\left[1+\kappa\tau - \frac{\tau}{T}\left(1 - e^{\frac{T}{\tau}(1+\kappa\tau)}\right)\right] + (1+\kappa\tau)^2\right\}}{(1+\kappa\tau)^3}. \quad (25)$$

Unlike diffusion, the influences only higher cumulants of photon count numbers, triplet corrections also shift the first cumulant by the factor $I/(1+\kappa\tau)$.

$$c_{app}^{(trip)}(T)q_{app}^{(trip)}(T) = \frac{cq}{1+\kappa\tau}, \quad (26)$$

$$c_{app}^{(trip)}(T)q_{app}^{(trip)}(T)^2 = \frac{cq^2\Gamma_{trip}(T)}{1+\kappa\tau}.$$

Solving these equations with respect to $q_{app}^{(trip)}$ and $c_{app}^{(trip)}$ yields $$c_{app}^{(trip)}(T) = \frac{c}{\Gamma_{trip}(T)(1+\kappa\tau)}, \quad (27)$$

$$q_{app}^{(trip)}(T) = q\Gamma_{trip}(T). \quad (28)$$

Now, having solved the problems with diffusion and triplet transitions separately, one shall study the joint problem. Usually, the time scale of triplet transitions is much shorter than that of diffusion. Therefore, one is justified to replace c and q in Eqs. 21 and 22 by $c_{app}^{(diff)}$ and $q_{app}^{(diff)}$. This lets one combine Eqs. 21, 22, 27, and 28 to express $c_{app}$ and $q_{app}$ as $$c_{app}(T) = \frac{c}{\Gamma_{trip}(T)\Gamma_{diff}(T)(1+\kappa\tau)}, \quad (29)$$

$$q_{app}^{(trip)}(T) = q\Gamma_{trip}(T)\Gamma_{diff}(T).$$

After having derived these expressions for $c_{app}$ and $q_{app}$, the data simulations and the experiments should verify their validity.

Taking into consideration the foregoing comments, the present invention relates in a general aspect to a method for characterizing samples having fluorescent particles, comprising the steps of:

monitoring intensity fluctuations of fluorescence emitted by the particles in at least one measurement volume by detecting sequences of photon counts by at least one photon detector, determining from the sequences of photon counts intermediate statistical data comprising at least two probability functions, $\hat{P}_1(n_1)$, $\hat{P}_2(n_2)$, ..., of the number of photon counts, $n_1, n_2, \ldots$, detected in different sets of counting time intervals, determining from said intermediate statistical data a distribution of particles as a function of at least two arguments, wherein one argument is a (measure of) specific brightness of the particles and another argument is a (measure of) diffusion coefficient of the particles.

In a preferred embodiment, the diffusion coefficient of a particle can be determined. It might however be also advantageous to use a measure which describes the diffusion of particles, e.g. diffusion time. The equivalent considerations apply to specific brightness, or a measure thereof.

Generally speaking, the present invention therefore comprises the steps of (i) Optically sensing signals resulting from fluorescence emitted from fluorescent particles like e.g. molecules present in the sample, and (ii) Electronically processing the optically sensed signals, wherein said processing comprises the step of concurrent determination of specific brightness and diffusion times of said particles based on probability functions of photon counts detected in different sets of counting time intervals.

In a preferred embodiment, each set of counting time intervals consists of intervals of equal width while different probability functions $\hat{P}_{T_1}(n_1)$, $\hat{P}_{T_2}(n_2)$, ... correspond to counting time intervals of different widths $T_1, T_2, \ldots$. In principle, at least two distributions with different widths of the counting time interval are needed in order to obtain information about the diffusion, but it might be preferred to use more than two distributions for analysis.

In a further preferred embodiment, in each set of counting time intervals these intervals are consecutive in time. However in each set of counting time intervals these might also overlap.

It is particularly preferred that said distribution function of particles is determined by fitting the experimentally determined probability functions $\hat{P}_1(n_1)$, $\hat{P}_2(n_2)$ ... by corresponding theoretical probability functions $P_1(n_1)$, $P_2(n_2)$, ....

In a preferred embodiment, said intermediate statistical data are processed applying inverse transformation with regularization (ITR) or inverse transformation with constraints (ITC) or inverse transformation with both regularization and constraints (ITRC). Because of statistical errors and limited size of measured data, inverse transformation as such is often an ill-posed mathematical problem, characterized by wild oscillations in its outcome. ITR, ITC and ITRC stabilize the mathematical problem by looking for a "regular" (e.g. a smooth) or constrained solution, for example by minimizing the sum of squared deviations of statistical data and a function of the solution itself, penalizing "irregular", usually irreproducible structures in the outcome, or values having no physical meaning. An example of constraining is disallowing negative values for concentrations (For the method of ITR, see e.g. W. H. Press et al. Numerical recipes in C: the art of scientific computing, $2^{nd}$ edition, Cambridge University Press, 1992, p, 808, which is hereby incorporated by reference).

In a preferred embodiment, the theoretical distributions $P_1(n_1)/P_2(n_2)$, ... are calculated through their generating functions $$G_{p(n)}(\tilde{\xi}) = \sum_n \tilde{\xi}^n P(n).$$

In particular, said distribution function of particles can be determined by fitting the experimentally determined probability functions $\hat{P}_1(n_1)$, $\hat{P}(n_2)$, ... by corresponding theoretical probability functions $P_1(n_1)$, $P_2(n_2)$, ... which are preferably calculated through their generating functions $$G_{p(n)}(\xi) = \sum_n \xi^n P(n).$$

In calculations of the theoretical distributions $P_1(n_1)$, $P_2(n_2)$ ... the optical spatial brightness function $B(r)$ might be accounted for by a separately determined relationship between brightness $B$ and volume elements $dV$. Depending on the position of a particle in the measurement volume, the detected values of its specific brightness might vary. Especially in cases of high polydispersity of the sample and/or low specific brightness differences of the particles in the sample, it is preferred—in respect to the accuracy of the measured specific brightness values—to take the spatial brightness function of the optical set-up into account. The relationship between the spatial brightness $B$ and volume elements $dV$ can be expressed through a variable $x=\ln(B_0/B)$ by a relationship $$\frac{dV}{dx} = A_0(1 + a_1 x + a_2 x^2) x^{a_3},$$

where $B_0$ is maximum brightness and $A_0$, $a_1$, $a_2$ and $a_3$ are empirical parameters of the spatial brightness function.

In a preferred embodiment, the generating function is calculated using the expression $G(\xi)=\exp[\int dq c(q) \int d^3 r (e^{(\xi-1) qTB(r)}-1)]$, where $c(q)$ is the density of particles with specific brightness $q$, $T$ is the length of the counting time interval, and $B(r)$ is the spatial brightness profile as a function of coordinates.

In a further preferred embodiment, concentrations of particles are selected to be approximately one or less molecules per measurement volume. Experiments if performed at significantly lower concentrations than one particle per measurement volume would result in a slow acquisition of meaningful information because most of the data collection time is spent on waiting, i.e. with no particles in the measurement volume. In the other limit of an increasing high number of particles, photon count number distributions approach a Gaussian limit; therefore it is increasingly difficult to resolve contributions from different species.

Preferably, either an avalanche photodiode or a photomultiplier is used as a photon-detector. It should be remarked that utilization of a single detector to collect distributions using a set of different widths of the counting time interval is favourite due to its fastness. However, in some instances it might be preferred to use at least two photon detectors, monitoring fluorescence of different wavelenghts or polarization.

The method according to the present invention can be preferably applied in the conductance of homogeneous assays, i.e. mix-and-measure assays with no need of separation steps.

It can be e.g. applied in diagnostics, high throughput drug screening, biomedicine, optimization of properties of molecules and identification of specific cell populations.

According to the present invention, confocal techniques are particularly suited to monitor fluctuating intensity of fluorescence. They may be applied—as outlined above—to a wide field of applications, such as biomedicine, etc., The conjugate focal (confocal) technique is based on using a point source of light sharply focused to a diffraction-limited spot on the sample. The emitted light is viewed through a spatial filter (pinhole) that isolates the viewing area to that exactly coincident with the illuminating spot. Thus, the illumination and detection apertures are optically conjugated, with each other. Light originating from focal planes other than that of the objective lens is rejected, which effectively provides a very small depth of field. Therefore, in a particular preferred embodiment of the present invention, a confocal microscope is used for monitoring the intensity of fluorescence. In order to achieve a high signal-to-noise-ratio, it is useful to monitor fluorescence using an apparatus that comprises: a radiation source (12) for providing excitation radiation (14), an objective (22) for focussing the excitation radiation (14) into a measurement volume (26), a detector (42) for detecting emission radiation (30) that stems from the measurement volume (26), and an opaque means (44) positioned in the pathway (32) of the emission radiation (30) or excitation radiation (14) for erasing the central part of the emission radiation (30) or excitation radiation (14). It might be particularly preferred to use an optical set-up described in detail in FIG. 7.

The advantage of FIMDA (present invention) over FCS (prior art) is that the method yields genuine concentrations of components in the sample, instead of the products of concentration and brightness squared in FCS. Only the independent determination of at least one of the two specific brightness values enables FCS to determine two concentrations unambiguously. However, inexperienced users of FCS often silently assume equal specific brightness when resolving two components. This assumption can cause significantly biased results. FIMDA brings this issue to the focus of analysis.

Another advantage of the presented method is its versatility. If FCS (prior art) or FIDA (prior art) fail to detect a particular readout upon a biochemical reaction, FIMDA (present invention) might be able to succeed. The biochemical reaction is not necessarily limited to the binding of two components, but can be any chemical reaction of interest. The possibility of using only one detector for recording two physical characteristics in a single measurement makes FIMDA a very efficient method of analysis which saves precious assay development time.

Because two read-out parameters are recorded in one measurement preferably with one detector, the present invention is an efficient and reliable method of analysis. The introduction of the generation function facilitates data evaluation and makes the method a fast analytical tool. FIMDA is more universal applicable to biochemical assays than FCS and FIDA applied separately, because each assay component can be distinguished by both diffusion time and brightness. The statistical accuracy of determining the diffusion time in FIMDA is better or at least as good as in FCS.

The invention is illustrated by the following figures and examples, which are not intended to limit the scope of the invention.

Figure 1:
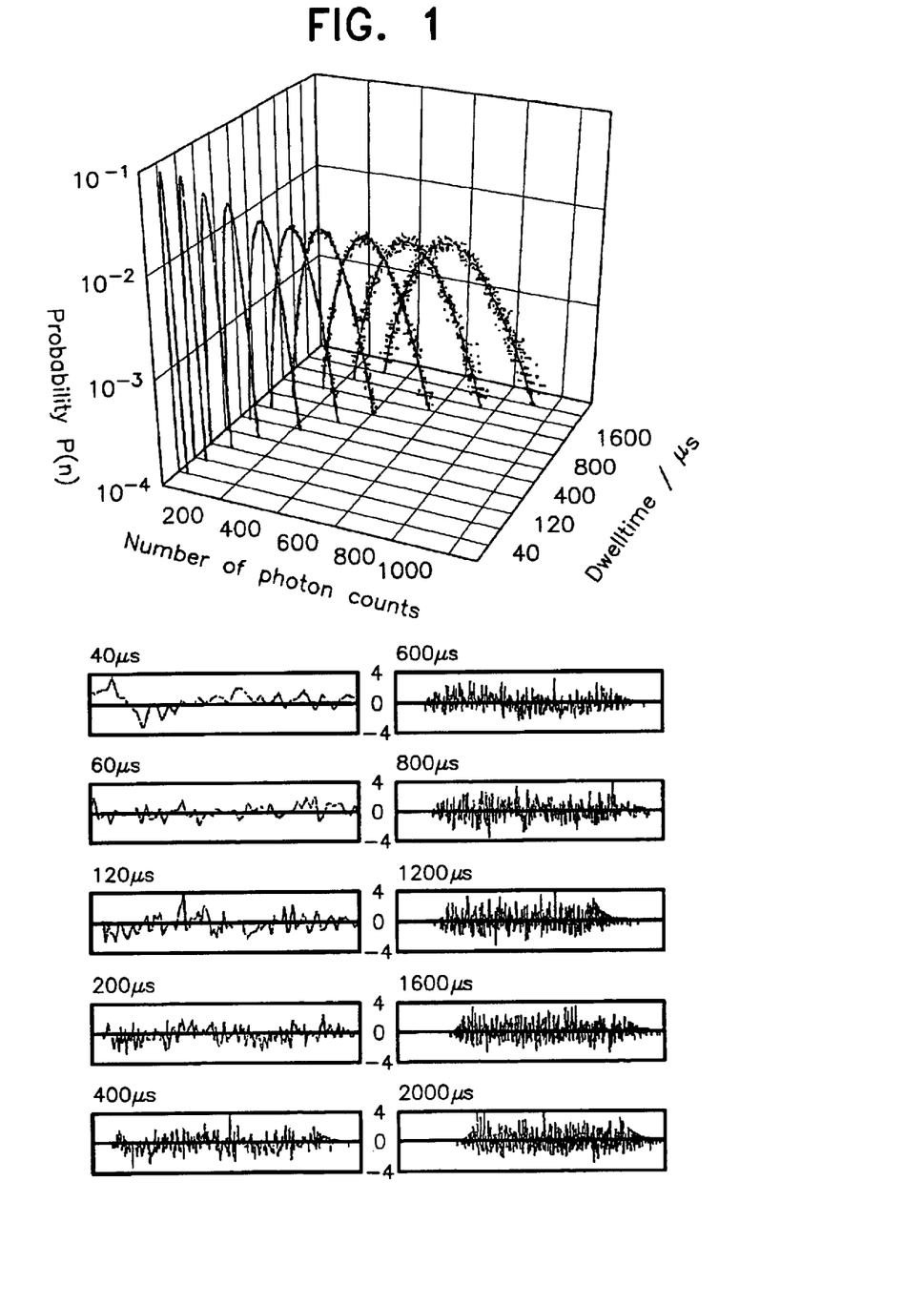
FIG. 1 illustrates the count number distributions and fits of a 3.8 nM Cy5 solution recorded simultaneously at different time windows T.

FIG. 1 illustrates the count number distributions and fits of a 3.8 nM Cy5 solution recorded simultaneously at different time windows T. The weighted residuals for the different time windows are shown in the lower part of the figure.

Figure 2:
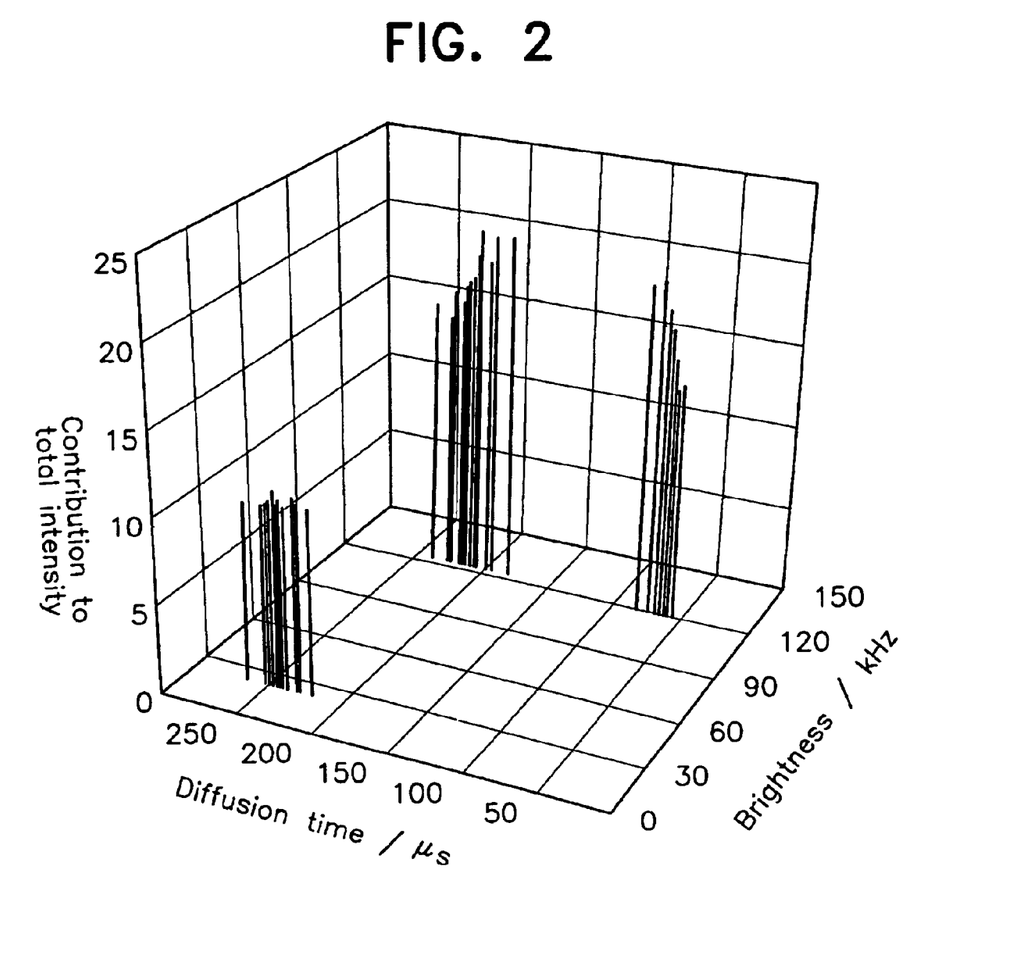
FIG. 2 illustrates the fitting results of simulated data for a mixture of 3 components.
Figure 3:
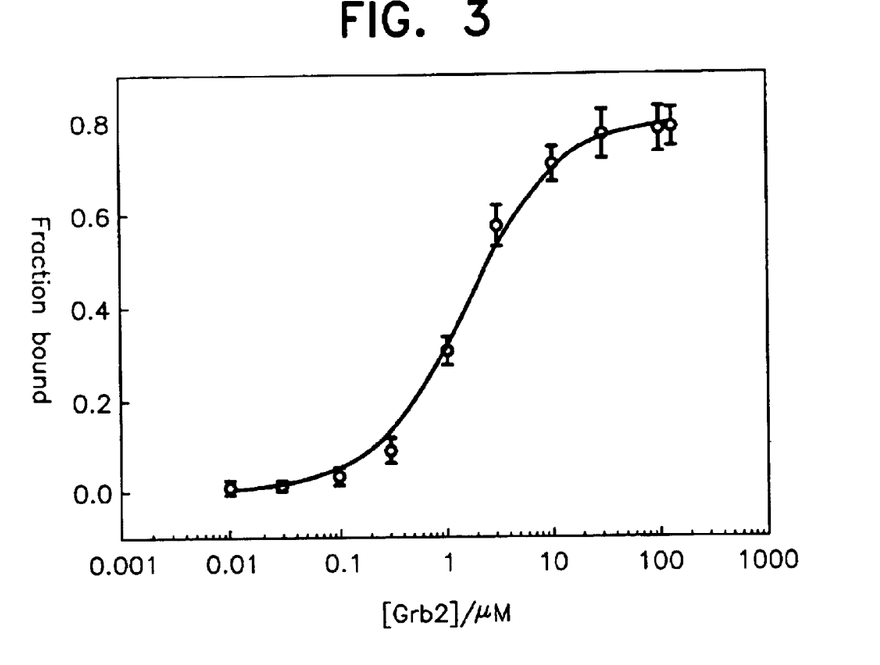
FIG. 3 illustrates the binding of pTyr-Val-Asn-Val-Lys (Cy5) to SH2.

FIG. 2 illustrates the fitting results of simulated data for a mixture of 3 components. The simulated brightness (in kHz) and diffusion time (in $\mu$s) values for the components are: (30 kHz, 192 $\mu$s); (120 kHz, 192 $\mu$s); (120 kHz, 64 $\mu$s). The contributions to the total intensity are 10.8 kHz. 20.4 kHz, and 14.4 kHz, respectively. The graph presents the results of FIMDA from 20 independent realizations of simulations, each corresponding to an experiment of 60 s duration, FIG. 3 illustrates the binding of pTyr-Val-Asn-Val-Lys (Cy5) to SH2. The solid curve results from a hyperbolic fit, yielding a binding constant of $K_D$=1.54±0.14 $\mu$M.

Figure 4:
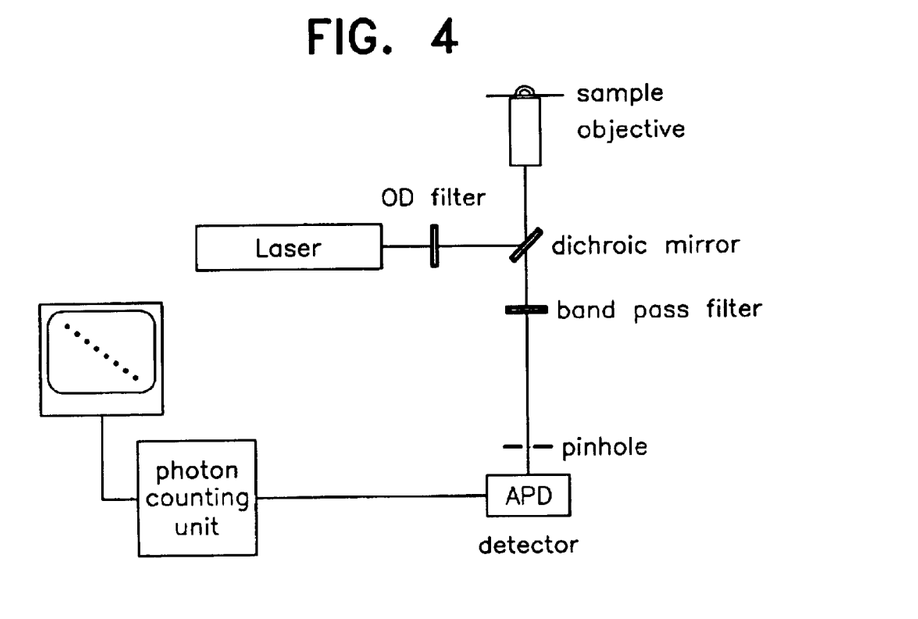
FIG. 4 illustrates the experimental setup used in Experiment 2.

FIG. 4 illustrates the experimental set-up used in Experiment 2. Radiation emitted by a laser passes an OD filter and reaches a dichroic mirror which reflects the radiation towards an objective having its focus within the sample under study. Fluorescence emitted from the sample passes the objective and reaches the dichroic mirror which is transparent for the fluorescent emission. After passing a bandpass filter and a pinhole, the emission reaches an avalanche photo-diode used as part of the detector. By means of a photon counting unit and a computer, specific brightness and diffusion can be determined according to the present invention.

Figure 5:
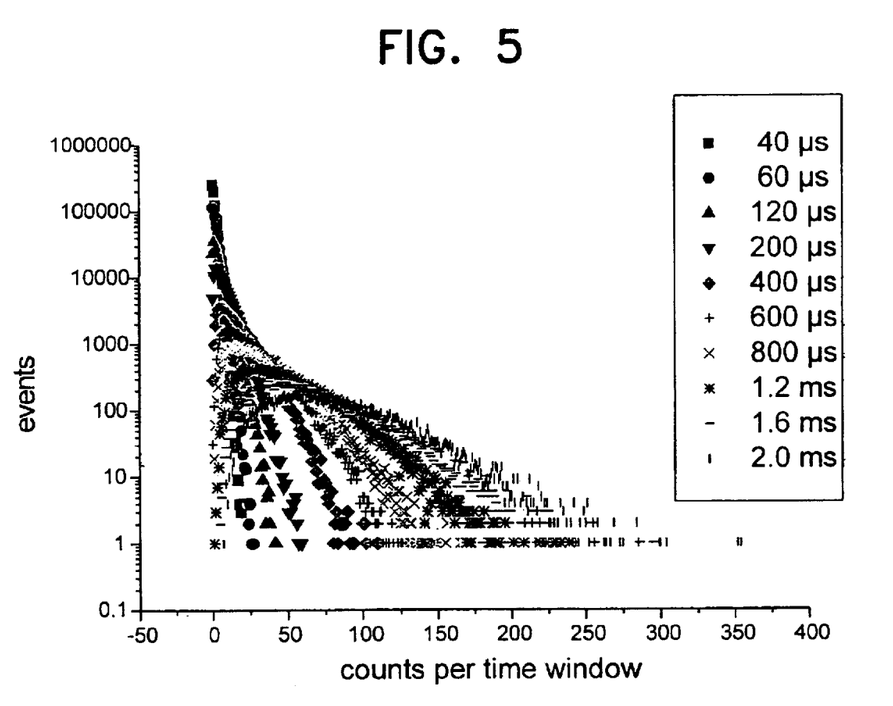
FIG. 5 shows 10 count number distributions with time windows 40, 60, 120, 200, 400, 600, 800, 1200, 1600 and 2000 $\mu s$ from a 0.8 nM Cy 5 solution.

FIG. 5 shows 10 count number distributions with time windows 40, 60, 120, 200, 400, 600, 800, 1200, 1600 and 2000 $\mu$s from a 0.8 nM Cy 5 solution.

Figure 6:
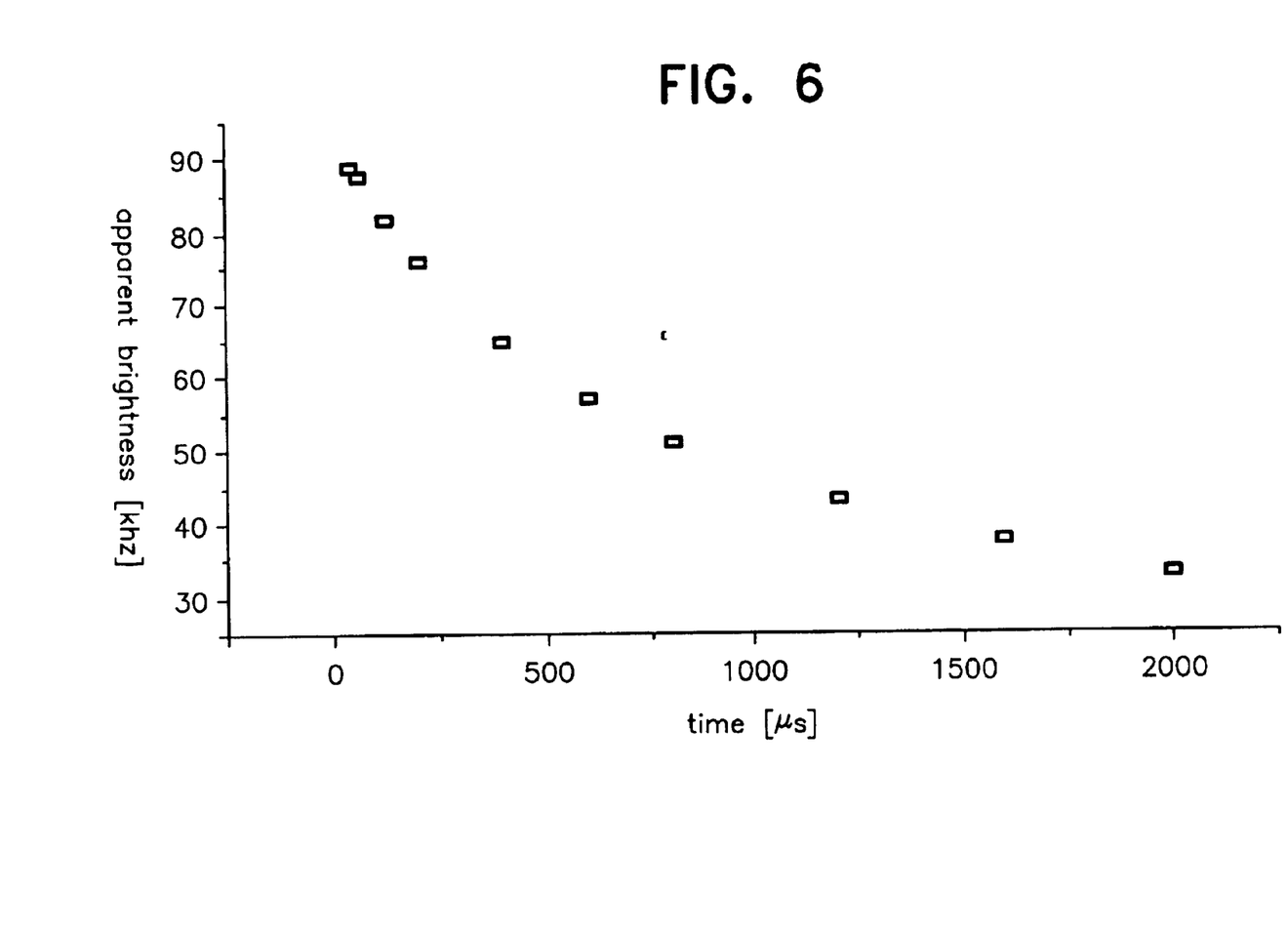
FIG. 6 shows the calculated apparent specific brightness of the dye as a function of counting time interval, evaluated by FDA.

FIG. 6 shows the calculated apparent specific brightness of the dye as a function of counting time interval, evaluated by FIDA.

Figure 7:
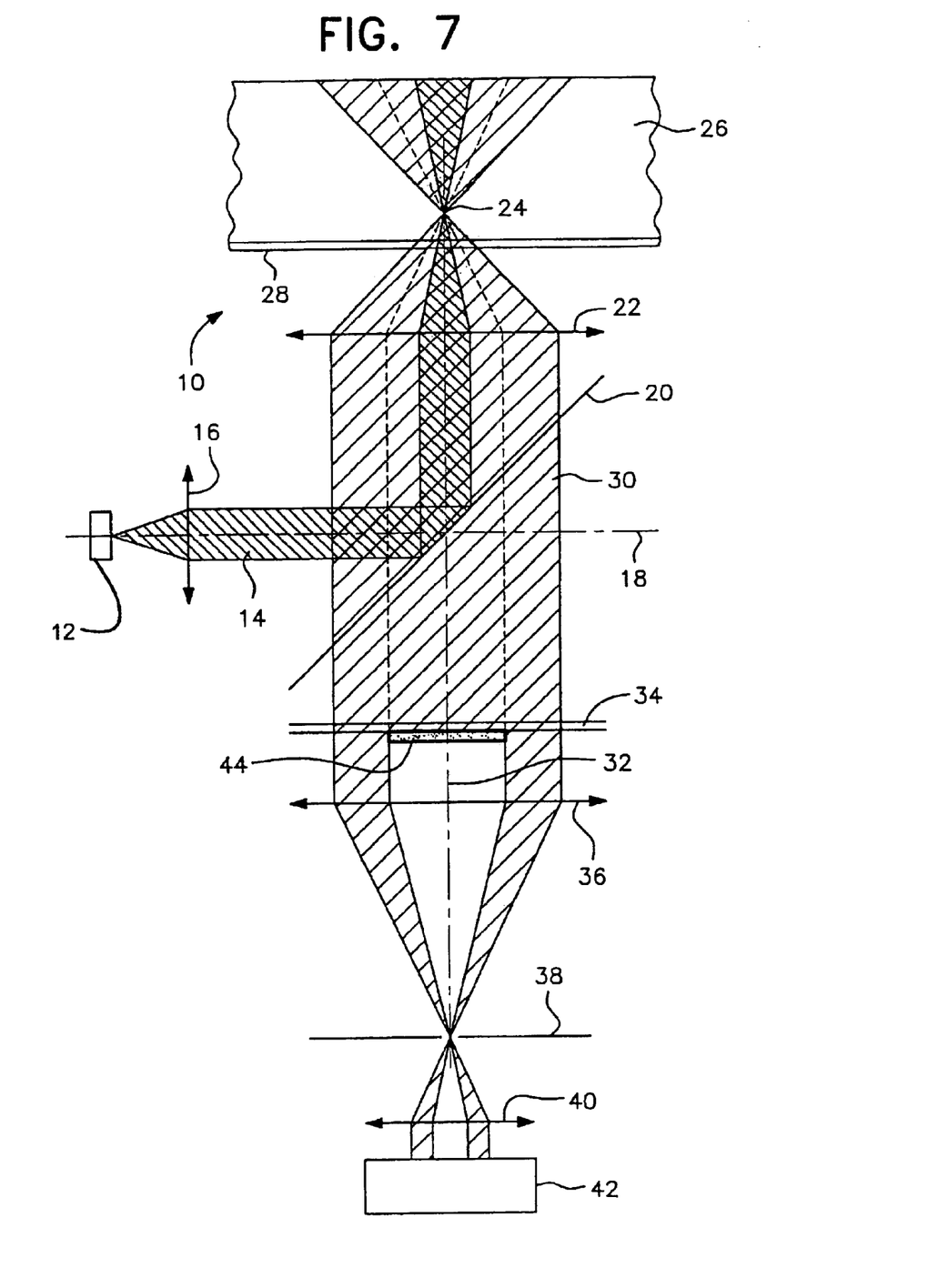
FIG. 7 shows one embodiment of an apparatus adapted for use in performing the method according to the nresent invention.

Reference is now made to FIG. 7 which shows one embodiment of an apparatus adapted for use in performing the method according to the present invention. Apparatus 10 comprises a laser 12 which serves as a light source for illuminating the sample by a bundle of coherent monochromatic excitation radiation 14. Excitation radiation 14 is paralleled by a lens 16 and reaches a dichroic mirror 20. Preferably, the angle between the optical axes 18 and the dichroic mirror 20 is 45°. The dichroic mirror 20 reflects the excitation radiation 14 in direction of an objective leas 22 having its focus 24 within a sample volume 26. Sample volume 26 and objective leas 22 are preferably separated from each other by a transparent cover glass 28, e.g. by the bottom of a commercially available micro-titer plate which houses the sample. The sample preferably includes fluorescently labeled molecules or other particles. Due to excitation by an appropriate excitation radiation 14, the molecules or other particles present in the sample emit radiation 30. Emission radiation 30 passes the objective lens 22 and reaches the dichroic mirror 20 which is transparent for emission radiation 30. Thereafter, emission radiation passes a filter 34 and a collimator lens 36 on the optical axis 32. A pinhole 38 is situated in the focus of collimator lens 36. Emission radiation 30 passing the pinhole 38 reaches a further lens 40 and, thereafter, is detected by the photo-detector 42. Within the pathway of emission radiation 30, in particular between dichroic mirror 20 and photo-detector 42, an opaque means 44 is provided through which a central part of the emission radiation 30 cannot pass. This central part of the emission radiation 30 stems from areas on the optical axes 32 in front of or behind the focus 24 of the excitation radiation 14. Only emission radiation 30 that stems from the focus 24 or its direct neighborhood passes the pinhole 38 and reaches photo-detector 42. Instead of placing an opaque means 44 within the pathway of emission radiation 30, the pathway of excitation radiation 14 is also suitable for positioning an opaque means 44. In particular, an opaque means 44 can be positioned between laser 12 and dichroic mirror 20. The use of an opaque means 44 in the method according to the present invention as described in detail herein improves the signal-to-noise ratio.

Experiment 1
Materials and Methods
Experimental Set-Up

The central optical part of the present FIMDA experiment is a confocal microscope as it is used in fluorescence correlation spectroscopy (Koppel et al., Biophys. J. 16: 1315–1329, 1976: Rigler et al., Eur. Biophys. J. 22: 169–175, 1993). For the excitation of fluorescence, a beam from a continuous wave laser is attenuated to ~800 $\mu$W by neutral density filters, passes a beam expander, and is directed to the microscope objective (UApo/340, 40x, N.A. 1.15, Olympus Optical Co. Ltd., Tokyo, Japan) by a dichroic mirror. Fluorescence is collected by the said objective through the dichroic mirror, a spectral band-pass filter, and is focused to a confocal pinhole, which serves to reject the out-of-focus light. The light, which passes the pinhole, is detected by a silicon photon counting module (SPCM-AQ-131, EG&G Optoelectronics, Vaudreuil, Canada). An electronic counter, constructed at EVOTEC as a computer plug-in card, collects the TTL pulses from the detector continuously and calculates the count number histograms for all preselected widths of time windows (40, 60, 120, 200, 400, 600, 800, 1200, 1600, 2000 $\mu$s) in real-time from the 32 MB onboard buffer. By feeding the detector outputs to a correlator, FCS measurements can be performed in parallel with FIMDA experiments.

In order to satisfy the spectral needs of the various fluorophores used in this study, different lasers and spectral band-pass filters were employed. For Cy5 (Amersham Pharmacia Biotech, Bucks, UK) conjugated bio-molecules an arrangement of a red laser diode (Crystal GmbH, Berlin, Germany; 635 nm) and a band-pass filter with a central wavelength of 670 mn (670DF40, Omega Optical, Brattleboro, Vt.) was used. In case of TAMRA (5-carboxytetramethylrhodamine) labeled molecules this was an arrangement of a frequency doubled Nd-YAG laser ($\mu$Green 4601; Uniphase, San Jose, Calif.; 532 nm) and a 590DF60 filter.

The effective dimensions of the illuminated volume were calibrated indirectly, using FCS on small dye molecules (TAMRA, Cy5) with known diffusion coefficients. The auto-correlation functions of diffusion were fitted to Eq. 17, i.e. assuming a 3-dimensional Gaussian intensity profile. The exact determination of the dimensions and profile would be very complex, since they are affected by both, the size of the laser beam as well as the size of the confocal pinhole. However, in most cases the knowledge of the exact dimensions is not necessary.

The focal beam radius was adjusted to ~0.75 $\mu$m by selecting an appropriate expansion factor of the original laser beam, resulting in a mean translational diffusion time of 360 $\mu$s for the free dye Cy5. This diffusion can be clearly observed when rising the time windows from 40 $\mu$s to 2 ms. As can be seen in FIG. 1, the selected count number distributions of a 3.8 nM Cy5 solution differ considerably. However, the major differences between the distributions are due to the varying mean count number in different time windows used. Diffusion of fluorescent molecules causes only small but significant modifications to the shape of each distribution.

The levels of background count rate are determined in a separate experiment on bidistilled water and amount usually to 0.5 kHz. The main contributor to this non-fluctuating background light intensity is Raman scattering from water.

Data Simulations

Real samples, comprising a mixture of molecules, which express deliberately chosen parameters (brightness values and diffusion coefficients), are difficult to prepare. Therefore, some evaluations of the new method were performed using simulated data. A number of sets of histograms for FIMDA, FIDA, and correlation functions for FCS have been simulated according to the following algorithm. In a closed rectangular reservoir, a given number of molecules is initially randomly distributed over a high number (typically 360×360×720) of discrete spatial grid points. Each molecule is subject to consequent diffusion simulation and jumps randomly by one grid unit either in x-, y-, or z-direction with a frequency corresponding to a given diffusion coefficient. The "focus" is located in the center of the reservoir, and the brightness distribution is assumed to be Gaussian in all three dimensions. When calculating the brightness integral from a molecule over a given set of time intervals, the molecule can be randomly trapped, as well as released from the triplet excited state (where it is dark). Now one can calculate an array of brightness integrals over basic time intervals of a given width (e.g. 5 $\mu$s) describing the evolution of the mixture. The brightness integrals are then converted into photon count numbers by generating a random Poisson number with the corresponding average. This step also accounts for the noise introduced by the detector because the random number generator is used not only for driving random motion of molecules but also for simulating random numbers of detected photons at given light intensities. The random count numbers obtained were subsequently used to calculate histograms for FIMDA and FIDA as well as the correlation function for FCS.

Due to the finite size of the simulation reservoir, some distortions of the correlation function (i.e., deviations from Eq. 17) can be expected. The distortions are in fact below the statistical noise level. Therefore, one can consider the simulations to be an adequate tool for estimating statistical errors of the extracted parameters. For this purpose, typically 30 realizations of experiments with a given set of molecular parameters were simulated, from which the standard deviations and the coefficients of variation (CV) as the ratio of standard deviation to mean value were calculated.

Fitting

A series of simultaneously measured or simulated distributions is globally fitted using a Marquardt algorithm. The fitting program is a modest modification of the program designed for FIDA (Kask et al., Proc. Natl. Acad. Sci. USA 96: 13756–13761, 1999). Theoretical distributions are calculated using exactly the same algorithm as in FIDA, except that each species has an individual apparent concentration and an apparent brightness at each time window, calculated according to Eqs. 29. All parameters not assigned to species but rather to the equipment (i.e. $A_0$, $a_1$, $a_2$, and $a_3$ from Eq. 5 and a from Eq. 20) are usually determined beforehand from separate adjustment experiments on pure dye solutions.

Biochemical System
The Grb2 (SH2)-phosphopeptide Interaction

Recent antitumor research has been focused on tyrosine kinase growth factor receptors (Levitzki, Eur. J. Biochem. 226: 1–13, 1994; Alessandro et al., Curr. Top. Microbiol. Immunol. 213: 167–189, 1996; Furet et al., J. Med. Chem. 41: 3442–3449, 1998). A critical link in the signal transduction pathway of this receptor is the interaction of its phosphotyrosine residue (pTyr) with the Src-homology 2 (SH2) domain of the adapter protein Grb2 (growth factor receptor-binding protein 2). For the recognition, a minimal peptide sequence of the receptor (pTyr-Val-Asn) is sufficient (Miller et al., J. Biol. Chem. 271: 16500–16505, 1996; Gram et al., Eur. J. Biochem. 246: 633–637, 1997; Furet et al., J. Med. Chem. 41: 3442–3449, 1998). The binding partner of this peptide motive, the SH2 domain of Grb2, can fold into a functional protein module independent of neighboring sequences (Booker et al., Nature, 358: 684–687, 1992; Overduin et al., Cell 70: 679–704, 1992). Therefore, as a model system, the bare SH2 domain (14.3 kDa) has been chosen to interact with a fluorescently labeled phosphopeptide (pTyr-Val-Asn-Val-Lys(Cy5)) (1387 Da).

The SH2 domain of Grb2 was prepared as described elsewhere (Lowenstein et al., Cell 70:431–442, 1992; Baumann et al., Eur. J. Immunol. 24: 1799–1807, 1994; Müller et al., J. Biol. Chem 271: 16500–16505, 1996). The phosphopeptide was synthesized using manual Fmoc solid phase chemistry and labeled with Cy5-NHS via a Lysine residue. An additional Valine was introduced to minimize possible interactions of the dye with the main recognition motive pTyr. The final compound, pTyr-Val-Asn-Val-Lys(Cy5) was characterized by mass spectrometry (LC/MS, and MALDI/TOF), UV/VIS, and fluorescence spectroscopy.

Results

Data Simulations and Test Experiments

At first, a series of measurements on a 1 nM TAMRA solution was performed collecting data in parallel for FIMDA as well as for FCS. This series of experiments, with duration of 2 s each, was repeated in simulation using similar molecular parameters. The purpose of these experiments was to verify whether simulations are a reasonable model of real experiments, in particular whether data simulations are a reasonable means of predicting statistical errors of estimated parameters. The coefficients of variation of the parameters extracted from simulated data indeed coincide with the results of the real experiment as can be seen in Tab. 1.

Another series of test experiments was repeated in a significantly shorter time domain with the goal to compare FIMDA and FCS in their ability lo estimate parameters of the triplet component. A set of counting time intervals of 2, 4, 8, 16, 32, 64, 128, 256, 512, and 1024 $\mu$s was selected for this purpose. The duration of these experiments was 16 s. The results, presented in Tab. 2, indicate that the values for the triplet parameters estimated by FIMDA have similar dependence on the excitation intensity to the FCS results. The FIMDA results are slightly biased and have higher CV values compared to FCS, since the estimation of triplet parameters in FIMDA is indirect, because the shortest time window (2 $\mu$s) is equal to the triplet lifetime. However, the main purpose of the triplet correction in the model is not to determine the triplet parameters, but to improve the quality of the fit and to remove a source of bias in the brightness and diffusion parameters.

Out of curiosity, histograms for FIMDA were simulated for three-component analysis. Two of the components had equal brightness values (120 kHz), and another pair had equal diffusion times (192 $\mu$s). Due to the larger number of free parameters, the simulated duration of experiments was increased to 60 s, so that the variations of fitted parameters stayed in reasonable limits. In this test, all parameters were subject to fitting The results are presented in FIG. 2 as vertical bars in a plane with brightness and diffusion time as x-y coordinates, and the ordinate displaying the contribution to the intensity, i.e., the product of concentration and brightness. The three components are clearly resolved, since the scatter in the location of individual bars is much smaller than the distance between the groups, which correspond to different components.

Note that with FIDA alone, the components with equal brightness cannot be resolved, while with FCS alone, the components with equal diffusion time remain unresolved.

Biochemical System

The experimental utilization of the new method will be demonstrated by the determination of the binding constant of the above introduced Grb2 (SH2)-phosphopeptide interaction. For this purpose a titration experiment was carried out keeping the pTyr-Val-Asn-Val-Lys(Cy5) concentration constant at 0.4 nM, while SH2 was subject to titration (0.01, 0.03, 0.1, 0.3, 1, 3, 10, 30, 100, and 130 $\mu$M). All experiments were performed under identical conditions, i.e., the same buffer (sterile filtered water, 50 mM Na-phosphate buffer pH 7.8, 50 mM NaCl, and 0.05% Pluronic; T=20° C.), and a data acquisition time of 30 s per measurement, repeated 30 times per sample. In each single measurement the same set of 10 different time windows was used (40, 60, 120, 200, 400, 600, 800, 1200, 1600, 2000 $\mu$s) resulting in 10 different photon count number histograms, which were globally fitted.

As the first step, the diffusion time $\tau_1$=407±6 $\mu$s and the specific brightness $q_1$=31.7±0.3 kHz were determined from a single component analysis applied to the pure conjugate solution. Addition of excess SH2 (130 $\mu$M) to 0.4 nM conjugate resulted in a sample with the majority of the conjugate bound to SH2. The complex was characterized both by a longer diffusion time and a higher specific brightness compared to the free conjugate. This mixture was then analyzed by all three methods (FIMDA, FIDA, and FCS) using a two-component fit with $\tau_1$ and/or $q_1$ fixed, depending on the method. The results of this step of analysis are presented in Tab. 3. It can be seen that all methods yield similar values of parameters for the complex. The corresponding CV values were again determined by two independent methods, i.e., from the statistical analysis of the results of a series of 30 measurements and from simulations. The two estimates of the statistical errors agree reasonably well and the CV values corresponding to different methods are similar, with the exception of FIDA, which has difficulties due to the small (30%) difference in specific brightness of the two components.

As the next step of the present studies, a sample with 3 $\mu$M SH2 was analyzed. This particular concentration was chosen to achieve a mixture of approximately equal proportions of complex and free conjugate. Since it is rather difficult to resolve components with only a twofold difference in diffusion coefficient and even smaller difference in specific brightness, here also the diffusion time and brightness of the complex were fixed to the values of Tab. 3. With the molecular parameters fixed, the concentrations were reliably determined by all methods. The results of this step of analysis are summarized in Tab. 4.

In the same manner, the whole series of SH2 concentrations was fitted. FIG. 3 shows the calculated fraction bound ($c_{complex}/(c_{complex}+c_{conjugate})$) for FIMDA with the solid curve resulting from a hyperbolic fit, that yielded a binding constant for the SH2-phosphopeptide interaction of $K_D$=1.54±0.14 $\mu$M. Comparable binding curves were also obtained by FCS and FIDA (data not shown), with $K_D$ values of 2.16±0.19 $\mu$M and 1.60±0.19 $\mu$M, respectively.

The data of FIG. 3 demonstrate that FIMDA is a suitable method for monitoring the formation of a molecular complex. FCS and FIDA experiments yielded similar $K_D$ values for this particular SH2-phosphopeptide interaction. In the literature the affinity is reported to vary by several orders of magnitude, depending on the peptide sequence (Müller et al., J. Biol. Chem. 271: 16500–16505, 1996; Gram et al., Eur. J. Biochem. 246: 633–637, 1997; Furet et al., J. Med. Chem. 41: 3442–3449, 1998). High affinities are in the range of $K_D$=10–100 nM. However, with a lysine (and Cy5 attached to it) at the +4 position of the phosphopeptide (defining p-Thr as the 0 position with '+' continuing on the C and '−' on the N terminus) the affinity decreases to the micromolar range. This result agrees well with the importance of lipophilic groups attached to 'appropriate' positions on the C-terminus, increasing the binding constant to the SH2-domain (Furet et al., J. Med. Chem. 41: 3442–3449, 1998). For example Val (at position pTyr+3) is making van der Waals contact with a large hydrophobic area on the SH2-domain.

One of the surprising results of this study according to the present invention is that in each of the experiments, the statistical accuracy of the diffusion time estimated by FIMDA is as good as or even better than that estimated by FCS. This is a counter-intuitive result because FCS is directly focused on fitting a diffusion-dependent correlation function G(t), while in FIMDA the diffusion time is estimated only indirectly, namely through the dependence of the apparent brightness on the width of the time window.

A further observation in this respect is that the CV values of the diffusion times are in general higher than those for the brightness values. This also holds true for the theoretical simulations and therefore reflects an effect rooting in the measuring principle. The phenomenon can be explained qualitatively by the different ways how these quantities are determined. For simplicity, one may imagine an observation volume with a constant brightness profile B(r) inside. In this case, one only needs to measure the average count rate of a molecule that enters the volume to determine its specific brightness. This requires the detection of many photons per given time interval but can in principle be achieved from a single passage. On the other hand, for estimating the diffusion time, one has to determine the mean duration of the diffusion driven passage, which inevitably requires averaging over many events, even though many photons may be detected each time. Therefore, in an experiment of fixed duration, the specific brightness of a molecule can in principle be determined with a higher accuracy than its diffusion time.

Experiment 2

FIG. 4 shows the experimental set-up used in this study. As an example for a typical measurement FIG. 5 shows 10 count number distributions with time windows 40, 60, 120, 200, 400, 600, 800, 1200, 1600, 2000 $\mu s$ from a 0.8 nM Cy 5 solution FIG. 6 shows the calculated apparent specific brightness of the dye as a function of counting time interval (time window), evaluated by FIDA. Since the diffusion time of the dye is long (compared to 40 $\mu s$) it spends only a short time in the confocal volume and its apparent brightness decreases. From this information the diffusion time can be calculated from a global fit.

The viability of the present invention was tested by measurements characterizing a ligand-protein interaction. The minimal peptide sequence pTyr-Val-Asn (originating from tyrosine kinase growth factor receptors) binds to the SH2-domain of the adapter protein Grb2. The conjugate pTyr-Val-Asn-Val-Lys(Cy5) was synthesized as binding partner for SH2. All measurements were performed under identical conditions (e.g. same buffer: sterile filter water, 50 mM Na-phosphate buffer pH 7.8, 50 mM NaCl and 0.05% Pluronic; T=20° C.). To obtain the $K_D$ value for the ligand protein interaction a titration experiment was carried out. The pTyr-Val-Asn-Val-Lys(Cy5) concentration was kept constant at 0.8 nM, while SH2 was subject to titration (0.01, 0.03, 0.1, 0.3, 1, 3, 10, 30, 100, and 130 $\mu M$). Each sample was measured 30 times keeping the acquisition time at 30 seconds per measurement. FCS (prior art), FIDA (prior art) and FIMDA (present invention) data were collected simultaneously in order to compare all three methods. Table 5 summarizes the results. It becomes clear that FIMDA is able to resolve both, the specific brightness and the diffusion time of both species (ligand and complex). Therefore, FIMDA is a more versatile tool than FCS or FIDA and will save assay development time. Comparing the standard deviations of all methods in determining brightness and diffusion time FIMDA is better or at least as good as FCS or FIDA.

Tables

TABLE 1

Comparison of coefficients of variation of estimated parameters from series of experimental and simulated histograms by FIMDA, and correlation functions by FCS.

| | | CV (%) | | | |
| --- | --- | --- | --- | --- | --- |
| | | FIMDA | | FCS | |
| Parameter | Mean value | Experimental data | Simulated data | Experimental data | Simulated data |
| Brightness q (kHz) | 115 | 2.5 | 2.3 | 2.6 | 2.5 |
| Concentration c (molecules per confocal volume) | 0.73 | 3.1 | 3.8 | 3.8 | 4.0 |
| Diffusion time τ ($\mu s$) | 287 | 5.4 | 4.3 | 7.3 | 5.2 |

TABLE 2

Triplet parameters, estimated from a series of experiments on 1 nM TAMRA solution by FCS and FIMDA at two different excitation intensities. Excitation wavelength 532 nm, duration 16 s, time windows 2, 4, 8, 16, 32, 64, 128, 256, 512, and 1024 $\mu s$.

| Peak excitation intensity, (kW/cm$^2$) | FCS | | | | FIMDA | | | |
| --- | --- | --- | --- | --- | --- | --- | --- | --- |
| | Triplet lifetime ($\mu s$) | CV (%) | Triplet population | CV (%) | Triplet lifetime ($\mu s$) | CV (%) | Triplet population | CV (%) |
| 118 | 1.98 | 3.9 | 0.182 | 2.7 | 3.12 | 7.6 | 0.137 | 3.1 |
| 187 | 1.75 | 3.7 | 0.235 | 1.6 | 2.59 | 3.8 | 0.183 | 2.0 |

TABLE 3

Comparison of estimated parameters and their coefficients of variation at a high receptor concentration (130 μM). A series of 30 experiments of 30 s duration each was evaulated by FIMDA, FIDA and FCS. Brightness (in FIMDA and FIDA) and diffusion time (in FIMDA and FCS) of the free conjugate were independently determined and fixed to 31.7 kHz and 407 μs, respectively, in this analysis.

| Parameter | Method | Mean value from experiment | CV (%) | CV (%) from simulations |
|---|---|---|---|---|
| $c_{conjugate}$ (molecules per confocal volume) | FIMDA | 0.132* | 43* | 82* |
| | FIDA | 0.196* | 76* | 71* |
| | FCS | 0.052* | 99* | 120* |
| $c_{complex}$ (molecules per confocal volume) | FIMDA | 0.618 | 9.6 | 8.0 |
| | FIDA | 0.555 | 26.7 | 14.9 |
| | FCS | 0.710 | 7.9 | 12.6 |
| $q_{complex}$ (kHz) | FIMDA | 39.5 | 2.2 | 2.3 |
| | FIDA | 38.4 | 5.5 | 3.9 |
| | FCS | 36.4 | 3.7 | 3.4 |
| $\tau_{complex}$ (ms) | FIMDA | 0.913 | 6.9 | 4.6 |
| | FCS | 0.898 | 5.4 | 7.2 |

*out of 30 realizations, in 5 to 10 cases zero conjugate concentration was yielded by the fitting program (negative values are disallowed). This indicates that in this particular example the conjugate concentration could not be properly determined. However, for further data analysis only $q_{complex}$ and $\tau_{complex}$ are needed.

TABLE 4

Comparison of the estimated concentrations at an intermediate receptor concentration (3 μM). In addition to the brightness and the diffusion time of the free conjugate, also the brightness and/or the diffusion time of the complex were fixed here to values shown in Tab. 3

| Parameter | Method | Mean value from experiment | CV (%) | CV (%) from simulations |
|---|---|---|---|---|
| $c_{conjugate}$ (molecules per confocal volume) | FIMDA | 0.328 | 11.7 | 4.9 |
| | FIDA | 0.311 | 16.1 | 4.9 |
| | FCS | 0.303 | 8.4 | 8.0 |
| $c_{complex}$ (molecules per confocal volume) | FIMDA | 0.437 | 8.2 | 3.4 |
| | FIDA | 0.455 | 10.0 | 3.7 |
| | FCS | 0.467 | 7.8 | 8.8 |

TABLE 5

Comparison of FIMDA (present invention) with prior art FCS and FIDA with respect to the determination of q, τ and $K_D$

| | $q_1$ [kHz] | $q_2$ [kHz] | $\tau_1$ [ms] | $\tau_2$ [ms] | $K_D$ [μM] |
|---|---|---|---|---|---|
| FIMDA | 31.7 ± 0.32 | 39.6 ± 0.9 | 0.402 ± 0.006 | 1.01 ± 0.08 | 1.68 ± 0.27 |
| FCS | | | 0.402 ± 0.013 | 0.867 ± 0.057 | 2.26 ± 0.28 |
| FIDA | 32.1 ± 0.31 | 43.3 ± 2.3 | | | 1.70 ± 0.29 |

What is claimed is:

1. A method for characterizing samples having fluorescent particles, comprising the steps of:
   a) monitoring intensity fluctuations of fluorescence emitted by the particles in at least one measurement volume by detecting sequences of photon counts by at least one photon detector,
   b) determining from the sequences of photon counts intermediate statistical data comprising at least two probability functions, $\hat{P}_1(n_1), \hat{P}_2(n_2), \ldots$, of the number of photon counts, $n_1, n_2, \ldots$, detected in different sets of counting time intervals,
   c) determining from said intermediate statistical data a distribution of particles as a function of at least two arguments, wherein one argument is a specific brightness of the particles, or a measure thereof, and another argument is a diffusion coefficient of the particles, or a measure thereof,
   wherein said distribution function of particles is determined by fitting the experimentally determined probability functions $\hat{P}_1(n_1), \hat{P}_2(n_2), \ldots$ by corresponding theoretical probability functions $P_1(n_1), P_2(n_2), \ldots$ and
   wherein said theoretical probability distributions $P_1(n_1), P_2(n_2), \ldots$ are calculated as functions of apparent concentrations and apparent brightness which depend on the widths of the counting time intervals in the different sets.

2. The method according to claim 1 wherein, in calculations of the theoretical distributions $P_1(n_1), P_2(n_2), \ldots$, an optical spatial brightness function B(r) is accounted for by a separately determined relationship between brightness B and volume elements dV.

3. The method according to claim 2, wherein the relationship between the spatial brightness B and volume elements dV is expressed through a variable $x=\ln(B_0/B)$ by a relationship $$\frac{dV}{dx} = A_0(1 + a_1 x + a_2 x^2) x^{a_3},$$

where $B_0$ is maximum brightness and $A_0, a_1, a_2$ and $a_3$ are empirical parameters of the spatial brightness function.

4. The method according to claim 1 wherein each set of counting time intervals consists of intervals of equal width while different probability functions $\hat{P}_{T_1}(n_1), \hat{P}_{T_2}(n_2), \ldots$ correspond to counting time intervals of different widths $T_1, T_2, \ldots$.

5. The method according to claim 4, wherein the apparent concentration is calculated as $$c_{app}(T) = \frac{c_{app}(0)}{\Gamma(T)},$$

the apparent brightness is calculated as $$q_{app}(T) = q_{app}(0)\Gamma(T),$$

and Γ(T) is calculated as $$\Gamma(T) = \frac{1}{c_{app}(0)q_{app}^2(0)T^2} \int_0^T dt_1 \int_0^T dt_2 G(t_2 - t_1),$$

where G(t) denotes autocorrelation function of fluorescence intensity and T denotes the width of the counting time interval.

6. The method according to claim 1 wherein the counting time intervals in each set are consecutive in time.

7. The method according to claim 1 wherein, counting time intervals in each set overlap.

8. The method according to claim 1 wherein said intermediate statistical data are processed applying inverse transformation with regularization and/or constraints.

9. The method according to claim 1 wherein the theoretical distributions $P_1(n_1)$, $P_2(n_2)$, ... are calculated through their generating functions $$G_{p(n)}(\bar{\xi}) = \sum_n \bar{\xi}^n P(n).$$

10. The method according to claim 9, wherein the generating function is calculated using the expression $G(\xi)=\exp[\int dq c(q) \int d^3 r (e^{(\xi-1)qTB(r)}-1)]$ where c(q) is the apparent density of particles with specific brightness q, T is the length of the counting time interval, and B(r) is the spatial brightness profile as a function of coordinates.

11. The method according to claim 9, wherein said generating functions are calculated using the formula $$G_{P(n)}(\xi) = \exp\left[\sum_i c_i \int (e^{(\xi-1)q_i B(r)T} - 1)dV\right]$$

in which c is an apparent concentration and q is an apparent brightness which both depend on the width of the counting time interval T.

12. The method according to claim 1 wherein said distribution function of particles is determined by fitting the experimentally determined probability functions $\hat{P}_1(n_1)$, $\hat{P}_2(n_2)$, ... by corresponding theoretical probability functions $P_1(n_1)$, $P_2(n_2)$, ....

13. The method according to claim 12 wherein the theoretical probability functions $P_1(n_1)$, $P_2(n_2)$, ... are calculated through their generating functions $$G_{P(n)}(\xi) = \sum_n \xi^n P(n).$$

14. The method according to claim 1 wherein concentrations of particles are selected to be approximately one or less molecules per measurement volume.

15. The method according to claim 1 wherein said at least one photon detector is either an avalanche photodiode or a photomultiplier.

16. The method according to claim 1 wherein said at least one photon detectors are at least two photon detectors which are used for monitoring fluorescence of different wavelengths or polarization.

17. The method according to claim 1 wherein said fluorescent particles are characterized by applying an homogeneous fluorescence assay.

18. The method according to claim 1, wherein the intensity fluctuation of fluorescence emitted by the particles in said at least one measurement volume are monitored by detecting said sequences of photon counts using said at least one photon detector, said at least one photon detector being part of a confocal apparatus.

19. The method according to claim 18 wherein said confocal apparatus comprises:

a) a radiation source (12) for providing excitation radiation (14), b) an objective (22) for focusing the excitation radiation (14) into a measurement volume (26) of said at least one measurement volume, c) a detector (42) of said at least one photon detector for detecting emission radiation (30) that stems from the measurement volume (26), and d) an opaque means (44) positioned in the pathway (32) of the emission radiation (30) or excitation radiation (14) for erasing the central part of the emission radiation (30) or excitation radiation (14).

* * * * *